United States Patent
Kerns et al.

(10) Patent No.: US 10,485,620 B2
(45) Date of Patent: Nov. 26, 2019

(54) STERILE SURGICAL DRAPE FOR OPHTHALMIC SURGERY

(71) Applicant: Alcon Pharmaceuticals Ltd., Fribourg (CH)

(72) Inventors: Ralph Kerns, Laguna Niguel, CA (US); Mark Humayun, Glendale, CA (US); Matthew T. McCormick, Angelus Oaks, CA (US)

(73) Assignee: Alcon Pharmaceuticals, Ltd., Fribourg (CH)

( * ) Notice: Subject to any disclaimer, the term of this patent is extended or adjusted under 35 U.S.C. 154(b) by 0 days.

(21) Appl. No.: 14/419,926

(22) PCT Filed: Aug. 5, 2013

(86) PCT No.: PCT/US2013/053652
§ 371 (c)(1),
(2) Date: Feb. 5, 2015

(87) PCT Pub. No.: WO2014/025702
PCT Pub. Date: Feb. 13, 2014

(65) Prior Publication Data
US 2015/0238264 A1    Aug. 27, 2015

Related U.S. Application Data

(60) Provisional application No. 61/680,192, filed on Aug. 6, 2012.

(51) Int. Cl.
*A61B 46/00* (2016.01)
*A61B 46/23* (2016.01)
(Continued)

(52) U.S. Cl.
CPC ............. *A61B 46/00* (2016.02); *A61B 46/23* (2016.02); *A61B 50/20* (2016.02); *A61B 90/40* (2016.02);
(Continued)

(58) Field of Classification Search
CPC ....... A61B 19/08; A61B 19/088; A61B 46/20; A61B 46/23; A61B 46/27;
(Continued)

(56) References Cited

U.S. PATENT DOCUMENTS 2,165,615 A * 7/1939 Cope .................. B60H 1/00264
165/126
2,628,803 A * 2/1953 Krewson ............... A61M 16/06
128/200.24
(Continued)

FOREIGN PATENT DOCUMENTS

FR       2878428       6/2006
JP       5784912       5/1982
(Continued)

OTHER PUBLICATIONS

International Search Report in PCT/US2013/053652 dated Nov. 7, 2013 in 9 pages.
(Continued)

*Primary Examiner* — Kari K Rodriquez
*Assistant Examiner* — Camtu T Nguyen

(57) ABSTRACT

The disclosure herein provides methods, systems, and devices for a sterile ophthalmic surgical drape system that can provide a sterile operating field for use by a doctor, surgeon, nurse, and the like during ophthalmic medical procedures. The sterile field created by the drape system can allow a doctor, surgeon, nurse and the like to perform a medical procedure, such as ophthalmic surgery, outside of an operating room and in locations such as a doctor's office (Continued)

or a military operating room war setting. The sterile ophthalmic surgical drape system can comprise a drape, a frame apparatus, a hole of sufficient size for a microscope, a fan, a filter, air directors, and slits. The drape system can comprise a collapsible frame apparatus. The drape system may be configured to be used in conjunction with a surgical tray that houses pre-sterilized tools for use in a medical procedure.

9 Claims, 15 Drawing Sheets

(51) Int. Cl.
　　*A61G 7/05*　　(2006.01)
　　*A61G 13/10*　　(2006.01)
　　*A61B 90/40*　　(2016.01)
　　*A61B 50/20*　　(2016.01)
(52) U.S. Cl.
　　CPC ...... *A61B 2090/401* (2016.02); *A61G 7/0501* (2013.01); *A61G 13/101* (2013.01)
(58) Field of Classification Search
　　CPC ........ A61B 2046/201; A61B 2046/234; A47C 20/00; A47C 20/02; A47C 20/021; A47C 20/022; A47C 20/023; A47C 20/08
　　USPC ...................................... 128/849; 5/651, 637
　　See application file for complete search history.

(56) References Cited

U.S. PATENT DOCUMENTS

| | | | | |
|---|---|---|---|---|
| 3,820,536 A * | 6/1974 | Anspach | .............. | A61G 13/108 |
| | | | | 128/202.13 |
| 3,850,172 A | 11/1974 | Cazalis | | |
| 3,859,993 A * | 1/1975 | Bitner | .................... | A61G 10/04 |
| | | | | 128/200.24 |
| 4,122,848 A | 10/1978 | Carpel | | |
| 4,223,669 A | 9/1980 | Morledge | | |
| 4,275,719 A * | 6/1981 | Mayer | .................... | A61B 90/40 |
| | | | | 128/847 |
| 4,321,917 A * | 3/1982 | Campbell | ................ | A61G 7/05 |
| | | | | 128/200.24 |
| 4,550,713 A | 11/1985 | Hyman | | |
| 4,739,753 A * | 4/1988 | Brehm | .............. | A61M 16/0627 |
| | | | | 128/200.24 |
| 4,966,168 A | 10/1990 | Glassman | | |
| 5,140,997 A | 8/1992 | Glassman | | |
| RE34,512 E | 1/1994 | Dowdy et al. | | |
| 5,316,541 A | 5/1994 | Fischer | | |
| 5,322,072 A | 6/1994 | Harrison et al. | | |
| 5,488,944 A | 2/1996 | Kennedy | | |
| 5,503,163 A | 4/1996 | Boyd | | |
| 5,546,961 A * | 8/1996 | Harrison | ................ | A61B 90/40 |
| | | | | 128/849 |
| 5,611,551 A * | 3/1997 | Lin | .......................... | B25H 5/00 |
| | | | | 280/32.5 |
| 5,640,977 A | 6/1997 | Leahy et al. | | |
| 5,730,153 A | 3/1998 | Chang et al. | | |
| 6,065,808 A * | 5/2000 | Tinsley | .................. | A47C 9/005 |
| | | | | 297/195.11 |
| 6,199,551 B1 | 3/2001 | Kuslich | | |
| 6,500,199 B1 * | 12/2002 | Becker | ...................... | A61F 7/00 |
| | | | | 607/104 |
| 6,610,163 B1 | 8/2003 | Mathis | | |
| 6,810,880 B1 | 11/2004 | Jennings et al. | | |
| 6,843,252 B2 * | 1/2005 | Harrison | ............... | A61B 46/00 |
| | | | | 128/849 |
| 6,871,651 B2 | 3/2005 | Lanier | | |
| 6,899,668 B2 | 5/2005 | Paranjpe | | |
| 7,114,500 B2 | 10/2006 | Bonutti | | |
| 7,252,089 B1 * | 8/2007 | Birnbaum | .............. | A61B 46/00 |
| | | | | 128/853 |
| 7,886,743 B2 | 2/2011 | Cooper et al. | | |
| 8,001,632 B2 * | 8/2011 | Sanders | ............... | A47C 21/024 |
| | | | | 5/505.1 |
| 8,127,721 B2 | 3/2012 | Moran | | |
| 8,262,553 B2 | 9/2012 | Weston et al. | | |
| 8,555,892 B2 | 10/2013 | Traub | | |
| 8,568,391 B2 | 10/2013 | Kerns et al. | | |
| 2004/0058135 A1 | 3/2004 | Patel et al. | | |
| 2005/0227086 A1 | 10/2005 | Murphy | | |
| 2006/0149120 A1 | 7/2006 | Melles | | |
| 2006/0235436 A1 | 10/2006 | Anderson et al. | | |
| 2007/0064309 A1 * | 3/2007 | Luloh | .................... | A61B 46/10 |
| | | | | 359/510 |
| 2007/0221214 A1 * | 9/2007 | Brockman | ............. | A62B 17/04 |
| | | | | 128/201.25 |
| 2010/0174415 A1 | 7/2010 | Humayun et al. | | |
| 2010/0280436 A1 | 11/2010 | Self et al. | | |
| 2011/0220126 A1 | 9/2011 | Lebrette et al. | | |
| 2011/0290257 A1 | 12/2011 | Hillis et al. | | |
| 2011/0290689 A1 | 12/2011 | Baradarian et al. | | |
| 2011/0295193 A1 | 12/2011 | Fitzgerald et al. | | |
| 2012/0325704 A1 * | 12/2012 | Kerns | .................... | A61B 50/33 |
| | | | | 206/370 |

FOREIGN PATENT DOCUMENTS

| | | |
|---|---|---|
| JP | S9181152 | 10/1984 |
| JP | 2012-506291 | 3/2012 |
| WO | 2005/074854 | 8/2005 |
| WO | 2010/047703 | 4/2010 |

OTHER PUBLICATIONS

Office Action, Chinese Application No. 201380041647.2, with English translation; 10 pages, dated Jul. 25, 2016.
Office Action received for Chinese Patent Application No. 201380041647.2, with English translation, dated Feb. 15, 2017; 14 pages.
Office Action received for Chinese Patent Application No. 201380041647.2, with English translation, dated May 26, 2017; 13 pages.
Office Action received for Japanese Patent Application No. 2015-526610, with English translation, dated May 29, 2017; 8 pages.
Office Action for European Patent Application No. 13828524.2, dated May 22, 2018; 5 pages.
Extended European Search Report, Application No. 13828524.2; 7 pages, dated Mar. 17, 2016.

* cited by examiner

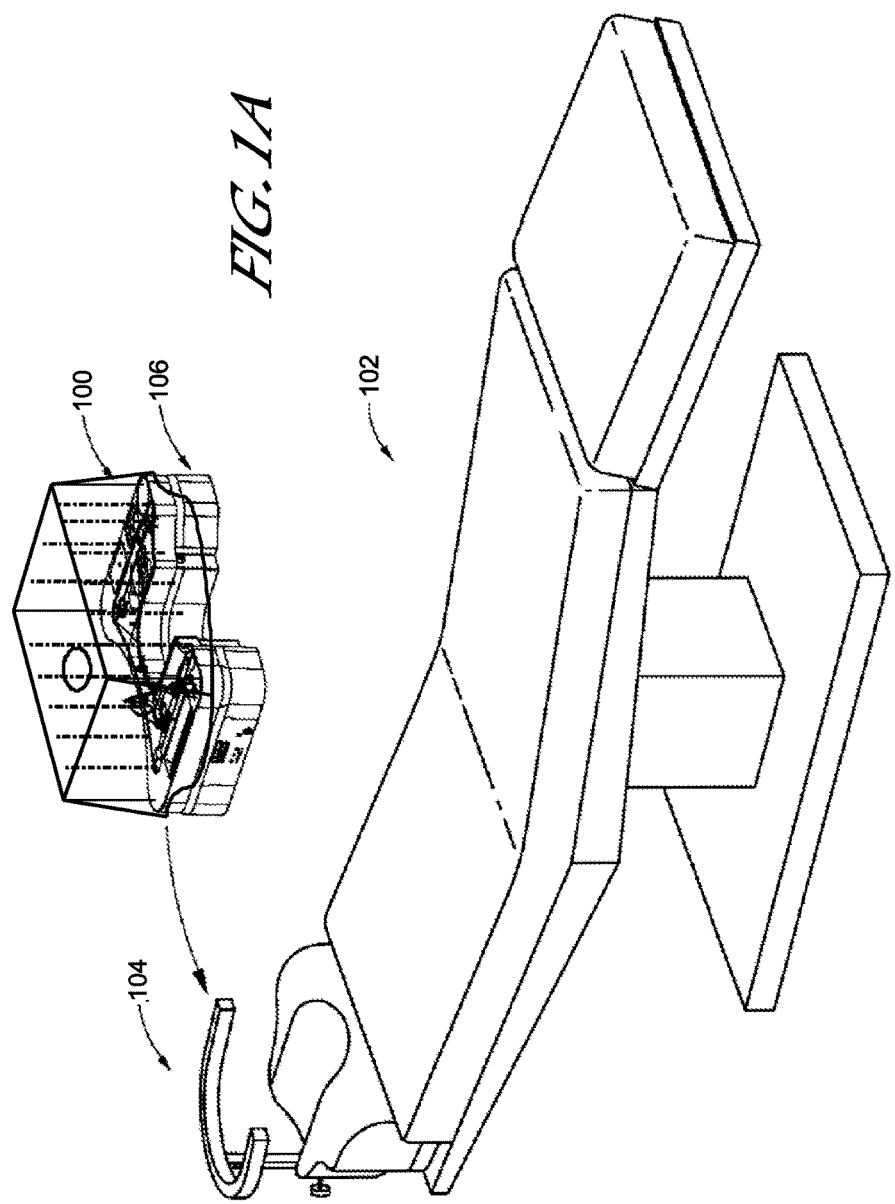

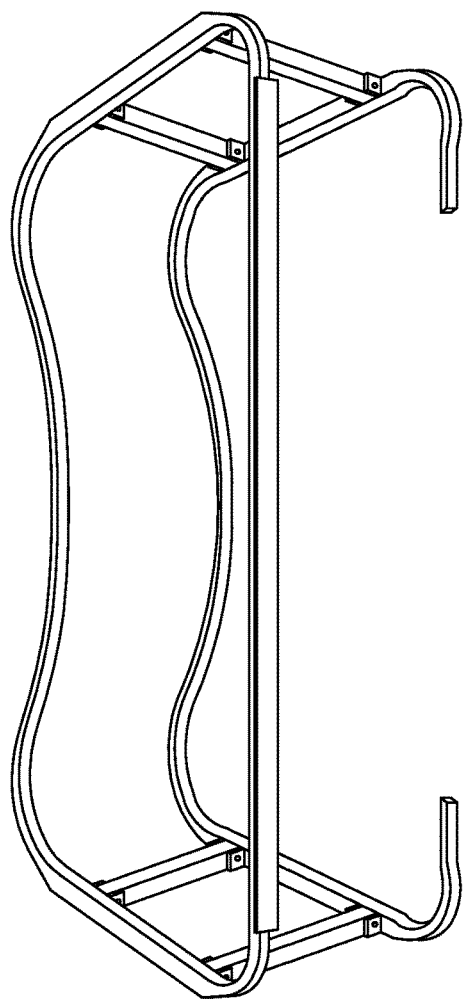

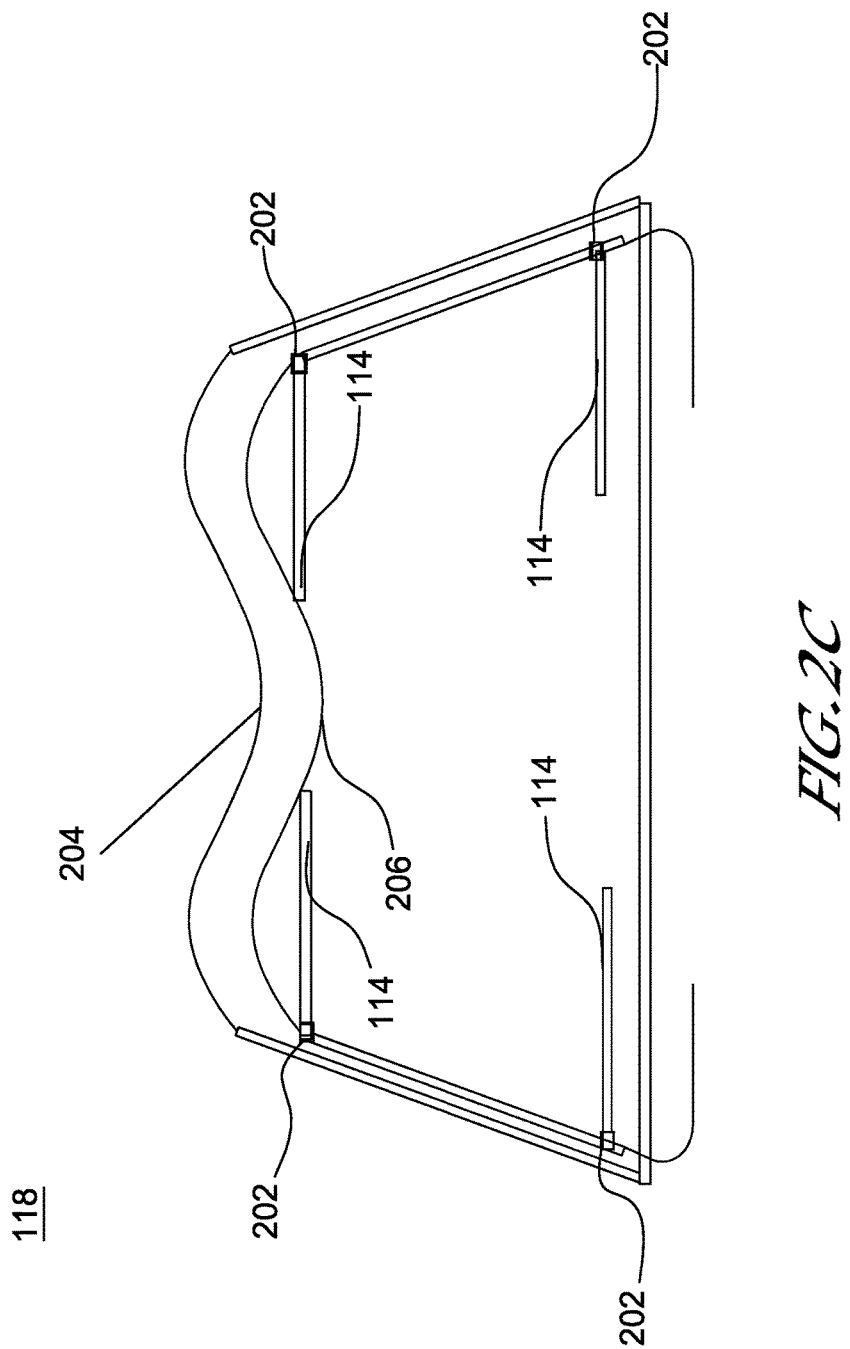

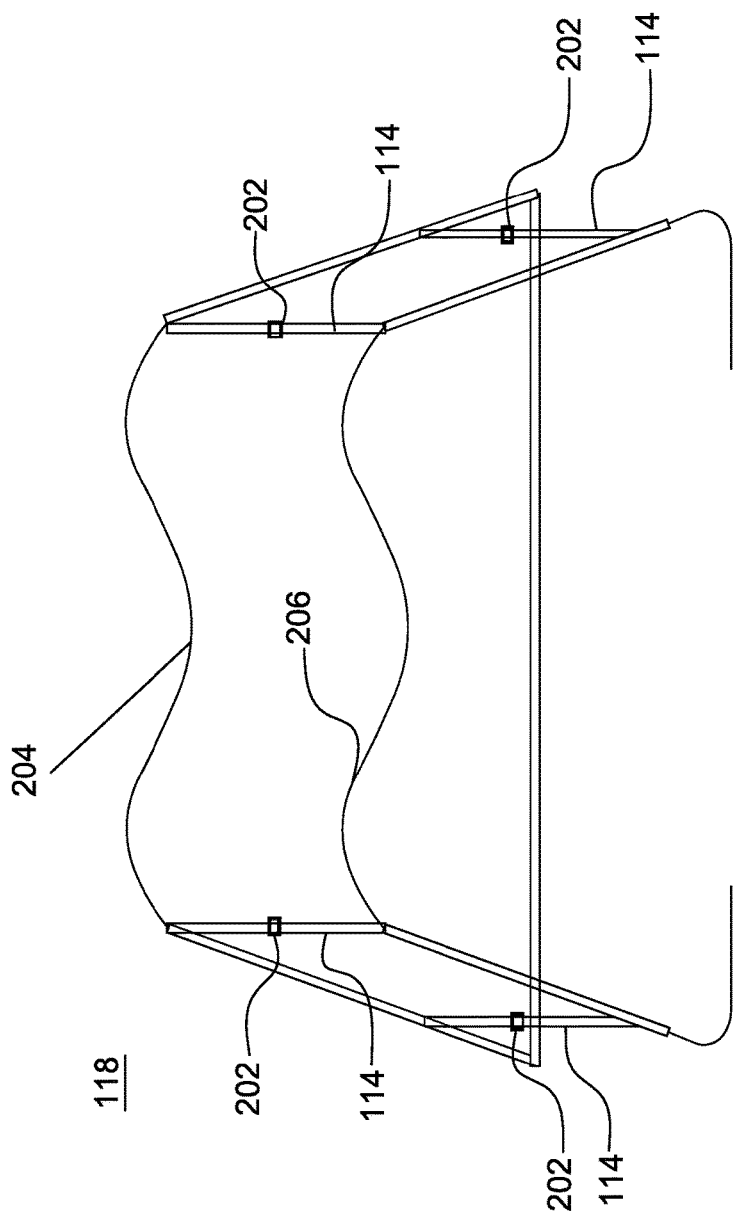

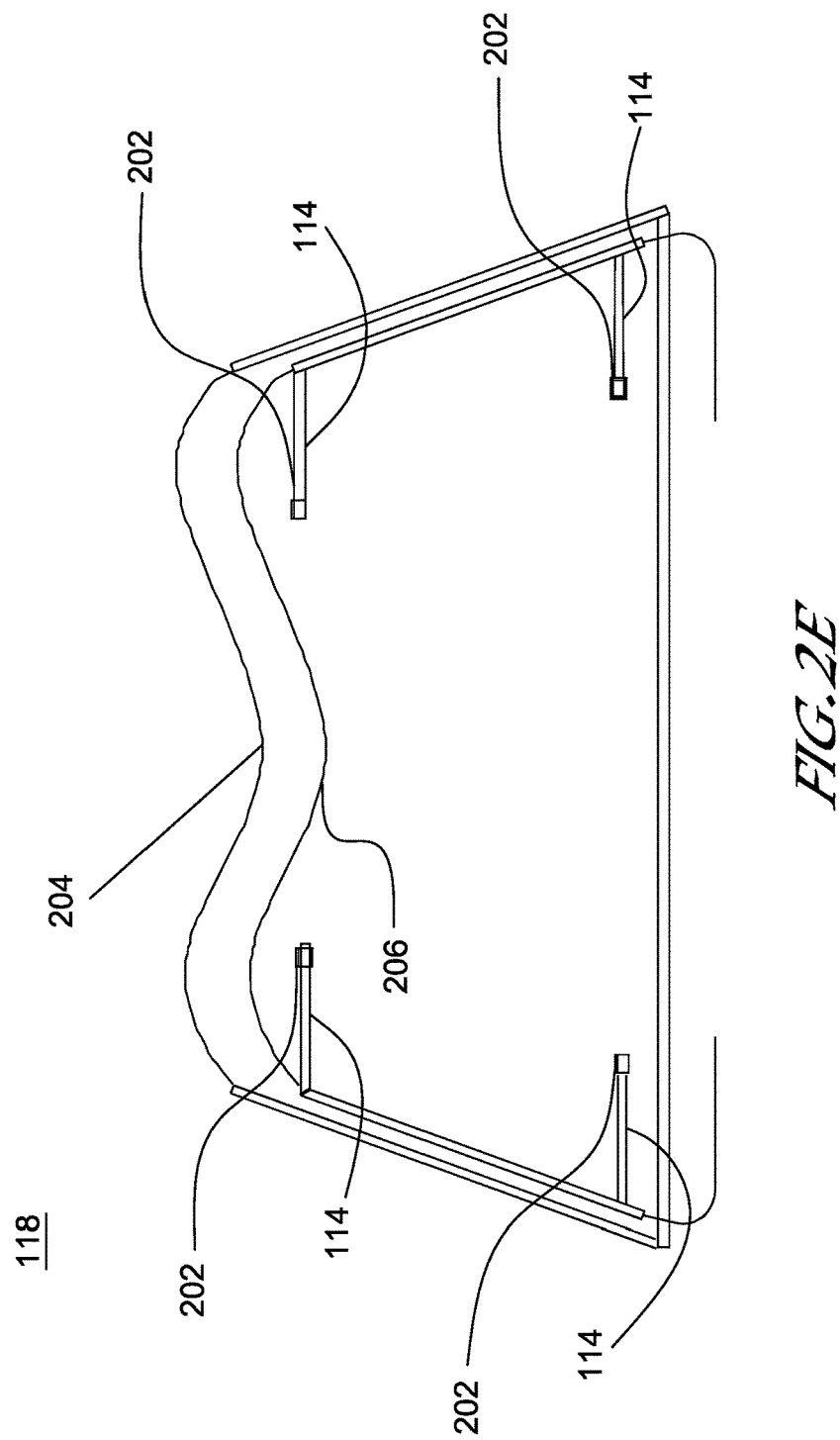

STERILE SURGICAL DRAPE FOR OPHTHALMIC SURGERY

RELATED APPLICATIONS

This application is a national stage application of International Patent Application No. PCT/US2013/053652, filed on Aug. 5, 2013, which claims the benefit of U.S. Provisional Application No. 61/680,192, filed on Aug. 6, 2012, titled "STERILE SURGICAL DRAPE FOR OPHTHALMIC SURGERY," which is hereby incorporated by reference herein in its entirety, including specifically but not limited to the devices, systems, and methods directed to a sterile surgical drape.

BACKGROUND

Field

The embodiments of the disclosure generally relate to ophthalmic surgery and more particularly to sterile ophthalmic surgical drape systems.

Description

With the development of new technologies, various types and kinds of drapes have been developed for ophthalmic surgical procedures. These drapes typically consist of a thin material that is placed on a patient and adheres to a patient's skin. Ophthalmic surgical drapes help isolate the surgical site from the adjacent facial structures, such as eyelashes, eyebrows, the nose, and the mouth. The material generally has a circular- or rectangular-shaped cutout through which a user such as a doctor, surgeon, or nurse may observe the eye and perform medical procedures. Despite the use of ophthalmic surgical drapes in medical procedures, doctors and surgeons are limited by when and/or where they may perform medical procedures because of the need for a sterilized operating field. A sterile field is generally established for many medical procedures, including ophthalmic surgery. Generally a sterile field refers to the surgical site as well as a surround area that specifies an area that is considered free from microorganisms. Such a sterile field can be used to prevent contaminants from infecting the eye during operation. Traditionally, a doctor or surgeon may only have access to a sterile operating field by scheduling a procedure in an expensive, sterilized operating room in a hospital.

SUMMARY

Advancements in ophthalmic surgical drape system technology make it possible to perform a medical procedure, such as ophthalmic surgery, in a sterile operating field outside of an operating room in locations such as a doctor's office or a military operating room war setting.

In accordance with one aspect, a device for performing surgery comprising: a drape, the drape comprising a hole configured to allow at least one accessory device to be placed in the hole and to access a surgical site covered by the drape; a frame, the frame comprising an upper rim, a lower rim, and one or more legs, wherein the one or more legs can connect the lower rim to the upper rim of the frame, wherein the drape is configured to be coupled to the frame to define an interior surgical chamber; and a fan, the fan configured to generate pressurized air within the interior surgical chamber, the fan comprising a filter, the filter configured to sanitize the pressurized air. In some embodiments, the fan is coupled to the frame. In some embodiments, wherein the drape is releasably coupled to the frame. In some embodiments, wherein the frame is collapsible. In some embodiments, wherein the one or more legs are configured to be deformable. In some embodiments, wherein the at least one accessory device comprises a microscope.

In some embodiments, wherein the fan is configured to generate a pressurized air of about 0.5 psi. In some embodiments, wherein fan is configured to generate a pressurized air of about 1 psi. In some embodiments, wherein the fan is configured to generate a pressurized air of about 2 psi. In some embodiments, wherein the fan is configured to draw air into the interior surgical chamber. In some embodiments, wherein the fan is configured to be located on a side portion of the frame. In some embodiments, wherein the fan is configured to be located on a top portion of the frame. In some embodiments, wherein the filter is configured to remove contaminants from the pressurized air. In some embodiments, wherein the fan comprises an air director, wherein the air director is configured to adjust the direction of an airflow of the fan. In some embodiments, wherein the drape further comprises at least one slit. In some embodiments, wherein the at least one slit provides an outlet for an airflow generated by the at least one fan to exhaust.

In some embodiments, the device further comprises a surgical tray, wherein the drape is configured to be coupled to the surgical tray, wherein the surgical tray is configured to be releasably attached to the drape. In some embodiments, wherein the surgical tray further configured to substantially form a seal between the drape and the surgical tray along one or more edges of the surgical tray. In some embodiments, wherein the surgical tray comprises a power source for powering the fan. In some embodiments, wherein the surgical tray comprises a control system for controlling the fan. In some embodiments, wherein the fan is positioned on the surgical tray.

In some embodiments, wherein the drape is configured to be positioned over a surgical patient platform. In some embodiments, wherein the surgical tray is configured to be coupled to a tray support. In some embodiments, wherein the tray support surrounds a surgical patient platform. In some embodiments, wherein the tray support is adjacent to a surgical patient platform. In some embodiments, wherein the tray support comprises a support bar, wherein the surgical tray is configured to be coupled to the support bar.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The foregoing and other features, aspects and advantages of the present invention are described in detail below with reference to the drawings of various embodiments, which are intended to illustrate and not to limit the invention. The drawings comprise the following figures in which:

FIG. 1A. depicts an example of one embodiment of a sterile surgical drape system configured to be used in conjunction with a surgical tray for ophthalmic surgery.

FIG. 2A-C. depicts an example of one embodiment of a frame of a sterile surgical drape system.

FIG. 2D-E. depicts an example of one embodiment of a frame of a sterile surgical drape system with legs.

DETAILED DESCRIPTION OF THE EMBODIMENTS

Figure 1B:
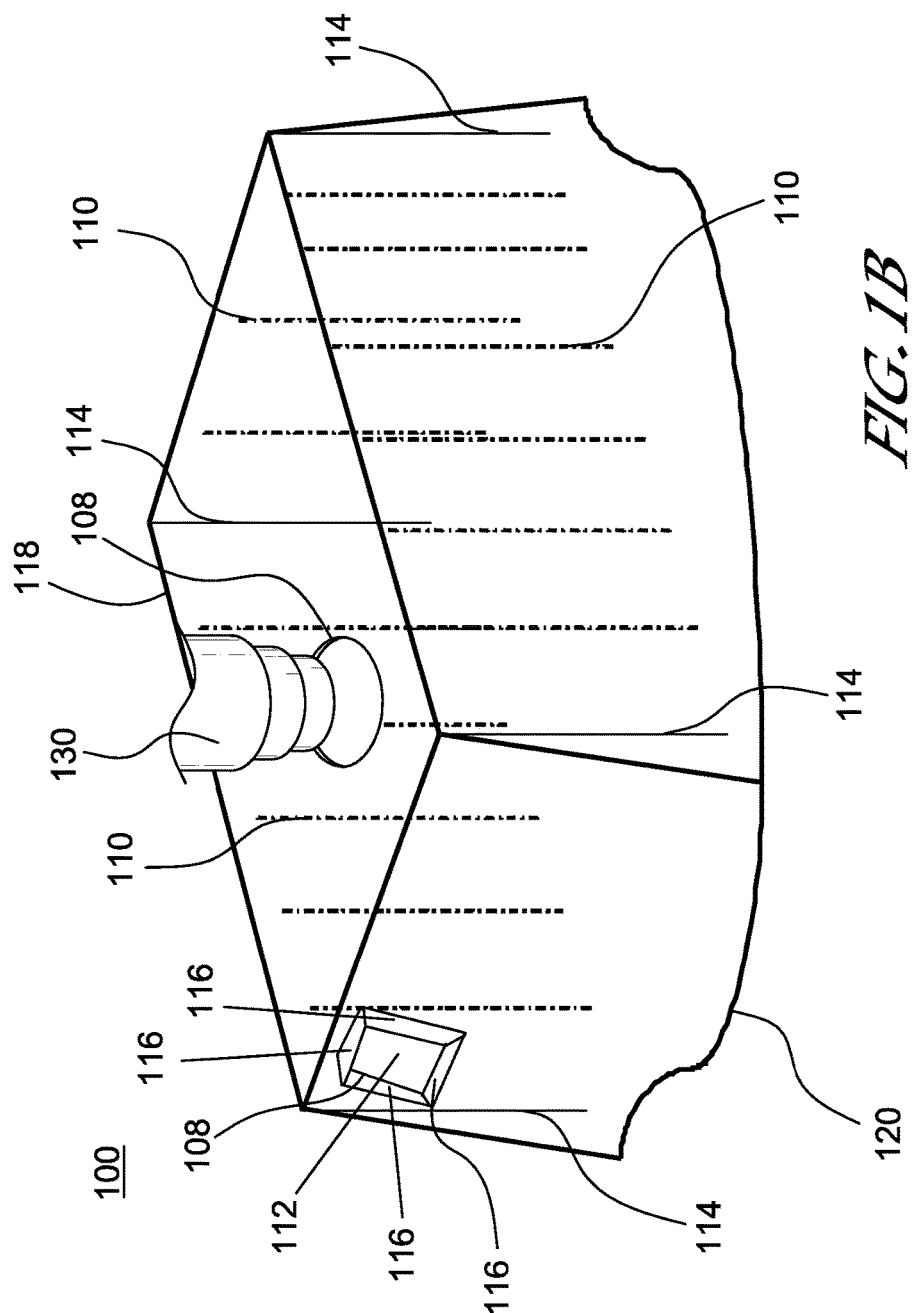
FIG. 1B. depicts an example of one embodiment of a sterile surgical drape system.

Embodiments of the invention will now be described with reference to the accompanying figures. The terminology used in the description presented herein is not intended to be interpreted in any limited or restrictive manner, simply because it is being utilized in conjunction with a detailed description of certain specific embodiments of the invention. Furthermore, embodiments of the invention may comprise several novel features, no single one of which is solely responsible for its desirable attributes or which is essential to practicing the inventions herein described.

As used herein, the term "drape system" is a broad term that can refer to a device or apparatus comprising a drape, a frame and/or additional features.

The disclosure herein provides methods, systems, and devices for performing ophthalmic surgery in a sterilized field. A sterile ophthalmic surgical drape system can beneficially provide a user, such as a doctor, surgeon, nurse, or assistant with a sterilized environment in which to perform a medical procedure. The ophthalmic surgical drape system can provide the sterile workspace and can be in a configuration that is ready to use after opening a frame and/or attaching a drape.

Use of a drape system can permit a medical procedure to be performed outside of an operating room by providing a sterile field. For example, a doctor, surgeon, nurse, assistant and the like can perform a procedure in nontraditional locations such as a doctor's office or a military operating room war setting.

The need for a sterile environment in which to perform surgery reduces the flexibility of users like doctors, surgeons, and nurses to operate in locations such as their own offices. Also, considerations of operating room economics become necessary to optimize operating room procedure throughput. As a result, doctors must schedule operation times in high-cost operating rooms, taking into account not just their own availability but those of the entire hospital. A sterile ophthalmic surgical drape system has the corresponding effects of decreasing the expensive costs associated with staffing and maintaining a sterilized operating room and increasing the number of procedures that practitioners can perform and the locations in which they may perform them, which constitute limiting factors in health care efficiency.

Surgical Drape System for Use in Surgical Procedures

In some embodiments, an ophthalmic surgical drape system is configured to be placed substantially over a patient's eye(s) and provide a sterile field underneath a drape. The ophthalmic surgical drape system can comprise a fan configured to generate a controlled airflow through the area underneath the drape to substantially prevent contaminants from entering the area underneath the drape.

In some embodiments, a drape system can be used alone and/or in conjunction with a sterile surgical tray and system. FIG. 1A illustrates one embodiment of a sterile ophthalmic surgical drape system 100 configured to be used in conjunction with a surgical tray 106 for ophthalmic surgery. In the depicted embodiment, a surgical drape system 100 is configured to be attached substantially above a surgical tray 106 to provide a sterile field underneath the surgical drape system 100. In some embodiments, the surgical drape system 100 drapes over the surgical tray 106 and substantially forms a seal along one or more edges of the surgical tray 106.

The combination of a drape system 100 and a surgical tray 106 can allow a doctor, surgeon, nurse, assistant and the like to perform an ophthalmic medical procedure in a sterile field outside of an operating room without having to acquire additional materials or assistance. Alternatively, a doctor, surgeon, nurse, assistant and the like may need a minimal amount of additional materials or assistance. In some embodiments, in addition to providing one or more surgical tools required for a medical procedure, the tray 106 can provide a power source and control systems for those tools, which are housed within the sterile surgical field created by the drape system 100.

In a medical procedure, such as ophthalmic surgery, a surgical tray 106 or at least one or more surfaces thereof can be part of the sterile field created by a sterile ophthalmic surgical drape system 100. In such a configuration, the surgical tray 106 can serve as a location on which to place or hold previously sterilized medical tools, instruments or medications. In some embodiments, by fitting an ophthalmic surgical drape system 100 on the circumference of a surgical tray and system 106, a user such as a doctor, surgeon, nurse, assistant, or the like can access all necessary surgical tools, instruments, or medications in a sterilized field in a fashion that has been tailored to be the most efficient organization for a medical procedure.

The surgical tray 106 can be of any type, currently known or to be developed in the future. For example, the surgical tray 106 can comprise sterile instruments and materials necessary for surgery to make them readily available to a nurse or surgeon. In certain embodiments, the surgical tray 106 can also comprise an electrical connector, a fluid connector, a pump, and/or control unit.

In some embodiments, the drape system 100 can attach to the surgical tray 106 via an attachment mechanism. For example, the attachment mechanism can comprise a screw, Velcro, mechanical interlocking, or the like. In certain embodiments, the attachment mechanism is permanent, semi-permanent, and/or temporary for easy assembly and/or disassembly. In some embodiments, the attachment mechanism is configured to sufficiently secure the drape system 100 such that it could not be lifted off the top of the patient inadvertently.

In some embodiments, the drape system 100 can be detached and lifted from the surgical tray 106 to allow a patient to be removed. In certain embodiments, the patient can be pulled out laterally through the sidewall of the drape system 100 without having to detach the drape system 100 from the surgical tray 106.

In some embodiments, a sterile ophthalmic surgical drape system 100 does not contact the patient in order to provide a user, for example, a doctor, surgeon, nurse, or assistant with maximum access to a patient's head. For example, in certain embodiments, the drape system 100 fits on the circumference of the tray and extends generally upward.

In some embodiments, a drape system 100 alone and/or in conjunction with a surgical tray 106 can be placed on top of or connected to a surgical chair 102, table, or the like. In other embodiments, the drape system 100 alone and/or in conjunction with a surgical tray 106 can be placed on top of or connected to an apparatus, such as a tray support 104, that surrounds or is adjacent to a surgical chair 102, table, or the like. In certain embodiments, the drape system 100 and tray 106 can be placed on or connected to a support bar of a tray support 104. The drape system 100 and surgical tray 106 can be placed on or connected to the apparatus, such as the tray support 104 or support bar of a tray support 104, in one of many different ways.

A tray support 104 or a support bar of the tray support can have a fixed or adjustable position relative to the surgical chair 102, table, or the like to which it is connected. A tray support 104 can be used for positioning the drape system 100 and tray 106 above a patient's head when the patient is lying on a surgical chair 102 or the like with his or her head positioned on a headrest. The tray support 104 can secure the sterile field of the drape system 100 in which a user, such as a doctor, surgeon, nurse, assistant or the like will be performing a medical procedure, such as an ophthalmic surgery.

A tray support 104 can surround a patient's head. This can act as a resting structure in the sterile field created by the drape system 100 on which a doctor, surgeon, nurse, assistant or the like may place his or her hands or arms during a medical procedure.

A support bar of a tray support 104 may have one of many different shapes. As depicted in one example of an embodiment in FIG. 1A, a tray support 104 may have a support bar with a U-shaped ring. In other embodiments, the support bar can be substantially circular, semi-circular, V-, or L-shaped, or a box with three sides.

A support bar of a tray support 104 may be manufactured from a substantially round or square bar, tube, or pipe. For example, as illustrated in FIG. 1A, a support bar with a U-shaped ring can be manufactured from a substantially square tube.

In some embodiments, a drape system 100, alone or in combination with a surgical tray 106, may be manufactured and shipped in a pre-sterilized package, for example through an ethylene oxide sterilization process, from a manufacturer to a customer, such as a hospital, doctor's office, military location, or the like. The drape system 100 can be used by a surgeon, doctor, nurse, assistant or the like to perform any medical procedure, including but not limited to ophthalmic surgery.

In certain embodiments, the entire drape system 100 is disposable after use, while in other embodiments, one or more individual components of the drape system 100 are disposable after use and one or more individual components are reusable. For example, the one or more individual components can include a pressurizing fan, frame leg(s), and drape, among others.

In some embodiments, a sterile surgical drape system 100 can comprise one or more features to provide a sterile environment and/or assist a medical procedure, such as ophthalmic surgery. For example, in some embodiments, a sterile surgical drape system 100 can comprise a hole in the drape for a microscope, a pressurizing fan, air directors, and/or slits in the drape among others. FIGS. 1B-1E illustrate different views of one embodiment of a sterile surgical drape system 100. In particular, FIG. 1B depicts a three-dimensional view of an example of one embodiment of a sterile surgical drape system 100.

In an embodiment, a sterile surgical drape system 100 comprises a frame 118 and a drape 120 placed over the frame. In some embodiments, the drape 120 is permanently, semi-permanently and/or temporarily attached to the frame 118 for easy assembly and/or disassembly. For example, the drape 120 can be glued to the frame 118. In other embodiments, the drape 120 is not glued but simply sits on top of the frame 118. The drape 120 is stabilized above the frame 118 as a result of friction between the drape 120 and the frame 118. In certain embodiments, the drape 120 is attached to the frame 118 via one or more mechanical features, including but not limited to a clip, hinge, perforation, or the like.

Drape

A surgical drape 120 may be provided over the patient during surgery to maintain a sterile surgical field. FIG. 1B illustrates an example of one embodiment of a sterile surgical drape system. The drape 120 may have a proximal side which faces the patient or patient support apparatus such as a chair or surgical table. The distal side of the drape faces upward toward the surgeons or medical professional. The drape 120 can be provided over a supporting structure or frame 118. The drape 120 can be a flexible or elastic material that conforms in shape to any shape of the frame 118. The frame 118 can have legs 114 as illustrated in FIG. 1B. The frame 118 and legs 114 can contact the proximal side of the drape and provide structure or support for the drape creating an interior chamber within the drape. For example, the drape can be provided over a rectangular frame and create a rectangular chamber where the walls and the top of the chamber are formed by the drape. Further, in some embodiments, the top surface of the drape and frame system can be formed of a Plexiglas or other rigid material. The bottom of the chamber can be open to the atmosphere and not covered by the drape. In some embodiments, the drape and frame can be provided over a surgical tray and thereby the bottom of the chamber can be enclosed or partially enclosed by the surgical tray as described in detail herein. The drape and frame system can be sealed entirely around the periphery to the tray. In some embodiments, the drape 120 and/or the frame 118 system can be sealed or substantially sealed to the surgical tray 106 as illustrated in FIG. 1H. In order to ensure that airflow out of the surgical chamber is through the hole 108, the area surrounding the patient's head 140, and the slits 110 and/or the openings for the hands of the surgeon and not through the drape-tray interface.

An ophthalmic surgical drape 120 may be manufactured from a variety of materials. For example, in some embodiments, a drape 120 may be manufactured from a transparent material, including but not limited to any transparent polymer. This can permit a user, such as a doctor, surgeon, nurse, assistant, or the like, to have optimum visibility during a medical procedure. In other embodiments, the drape 120 may be manufactured from an opaque material, such as cloth or opaque polymer. If an opaque drape 120 were used on the panels instead of a transparent drape, then the user's visibility may be limited. In some embodiments, the drape 120 may have one or more panels in the drape 120 manufactured from an opaque material and one or more panels in the drape 120 manufactured from a transparent material.

In some embodiments, the drape 120 may be disposable. In some embodiments the drape 120 may be a pre-sterilized drape 120 manufactured and shipped in a pre-sterilized package to a customer, such as a hospital, doctor's office, military location, or the like. For example, the drape 120 may be sterilized through an ethylene oxide sterilization process.

In some embodiments, the thickness of the drape 120 can be about 0.001 inches, about 0.002 inches, about 0.003 inches, about 0.004 inches, about 0.005 inches, about 0.006 inches, about 0.007 inches, about 0.008 inches, about 0.009 inches, about 0.010 inches, about 0.020 inches, about 0.030, about 0.040 inches, about 0.050 inches, about 0.060 inches, about 0.070 inches, about 0.080 inches, about 0.090 inches, about 0.100 inches, or any other thickness.

In certain embodiments, the drape 120 can further comprise one or more holes 118 for one or more microscopes, fans, filters, air directors, and/or slits, among others. The walls or sides of the drape can have slits 110 as illustrated in FIG. 1B. The slits 110 can be positioned vertically on the side of the drape. The slits 110 can allow a user to access the interior of the chamber formed by the drape. In some embodiments, the drape 120 can have a hole 108 provided through the drape 120. The hole 108 can also allow access to the interior of the drape chamber. The drape can be on the top and/or a side of the drape chamber. FIG. 1B illustrates a hole 108 positioned on the top of the drape 120. The hole 108 can be in the center of the drape or offset from the center depending on the intended use of the hole 108. In some embodiments, a hole 108 can be positioned on a side panel of the drape 120. The hole 108 can allow an accessory device to access the interior of the drape chamber. The accessory device can be a microscope, a fan, a surgical tool, an air director, a filter, or any accessory device as described herein. For example, as illustrated in FIG. 1B, a fan 112 can be positioned within a hole 108 in the dressing. The fan 112 can have air directors 116 operating in conjunction with the fan to provide a pressurized and directed airflow beneath the surgical drape and within the chamber as described in more detail herein.

Opening in Drape for Microscope

Regardless of whether a drape 120 is composed of a transparent and/or opaque material, it can be advantageous for a surgeon, nurse, or the like to visualize a surgical area underneath the drape via a microscope. The drape material even though translucent, can still create a view through the microscope that is unclear or obscured because of the material. Accordingly, in some embodiments, the drape 120 comprises one or more holes to allow a microscope(s) 130 to enter into the drape and/or view the surgical area without the obscuring effect of the drape as illustrated in FIG. 1B.

Figure 1C:
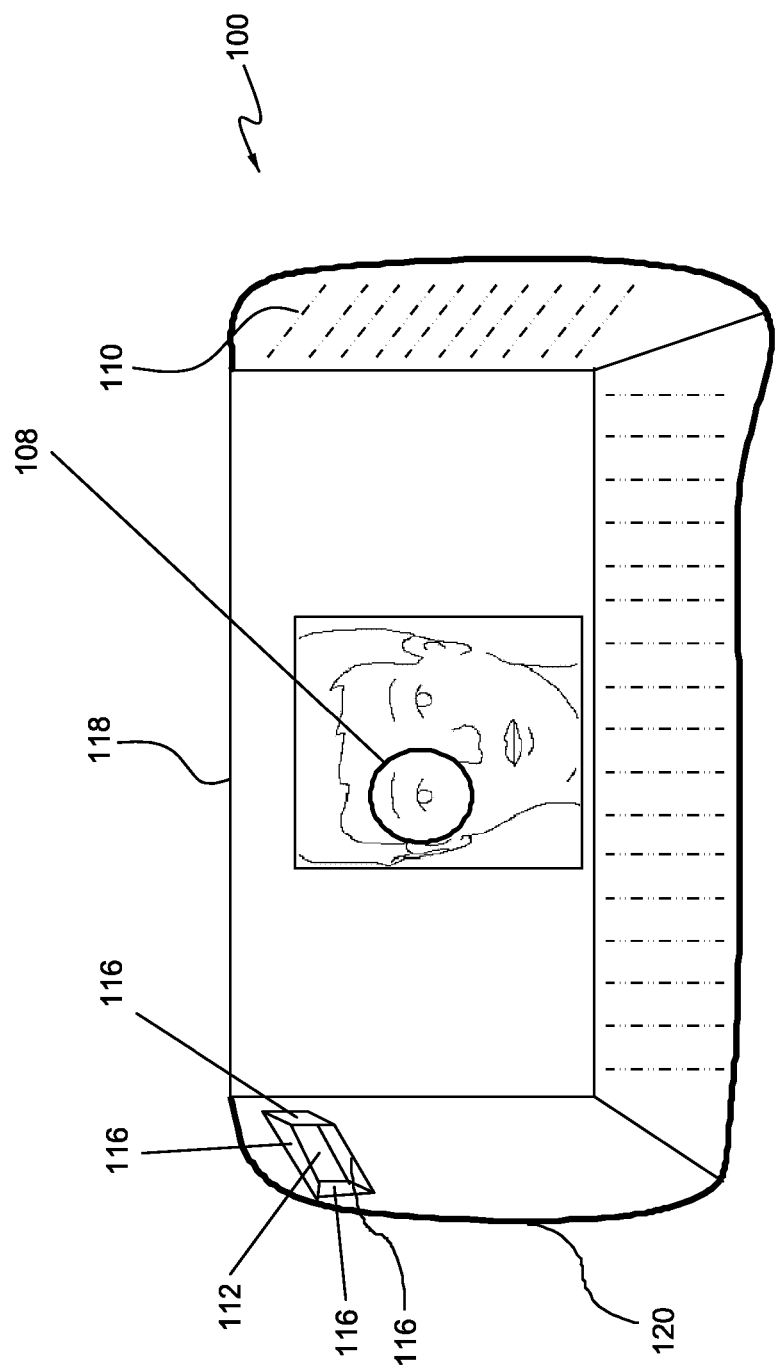
FIG. 1C. depicts a top view of an example of one embodiment of a sterile surgical drape system.

FIG. 1C shows a top view of a patient lying down on his or her back with an embodiment of the drape system 100 surrounding the head of the patient during a medical procedure. Such a patient can be prepared for any medical procedure, including for example an ophthalmic surgical procedure on one or both eyes of the patient.

In some embodiments, the drape 120 comprises one or more openings or holes 108 positioned over one or both eyes of the patient. The size of the hole 108 can be substantially the same size or larger than surgical microscopes that are generally used in ophthalmic surgery. A hole in the drape for the microscope 108 can permit visibility into the sterilized field by reducing a risk of reflections between, for example, a fiber optic in the eye and a drape material. In other embodiments, one or more openings for a microscope 108 can be positioned on any of the side surfaces or corners of the drape. In certain embodiments, the one or more openings are further configured to be used for insertion of other surgical tools.

Figure 2A:
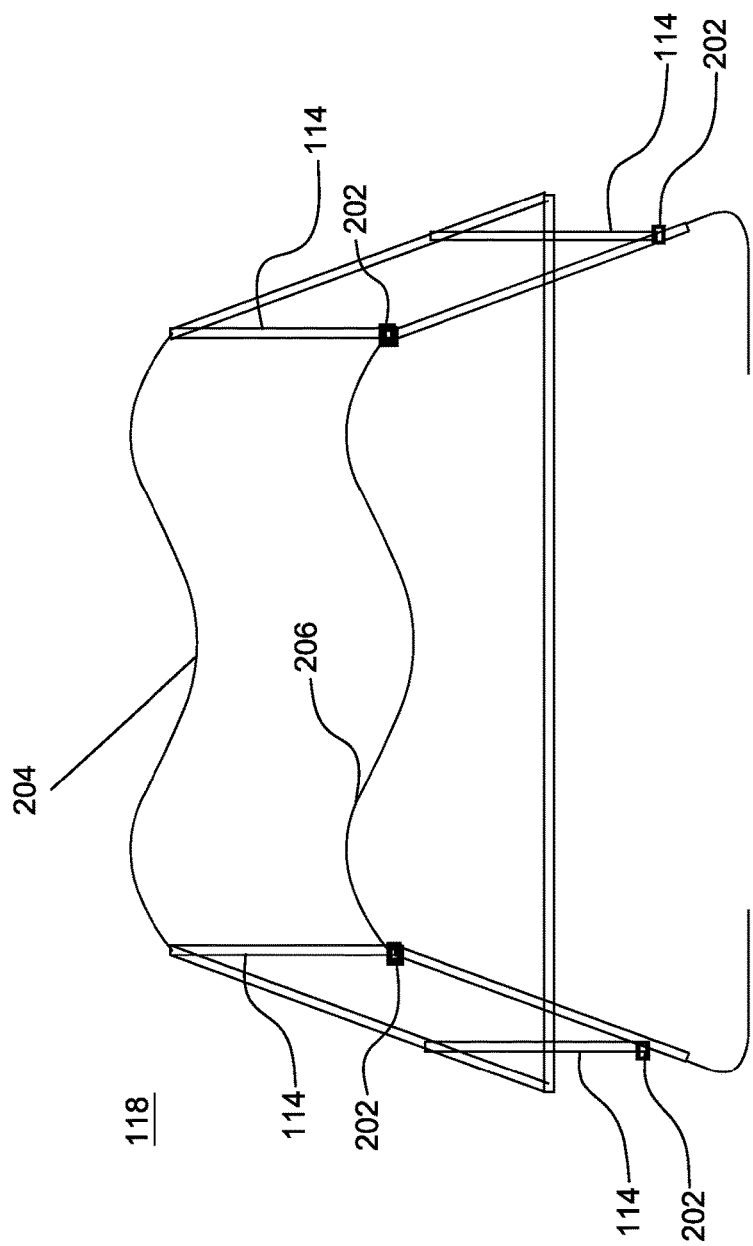
Figure 2F:
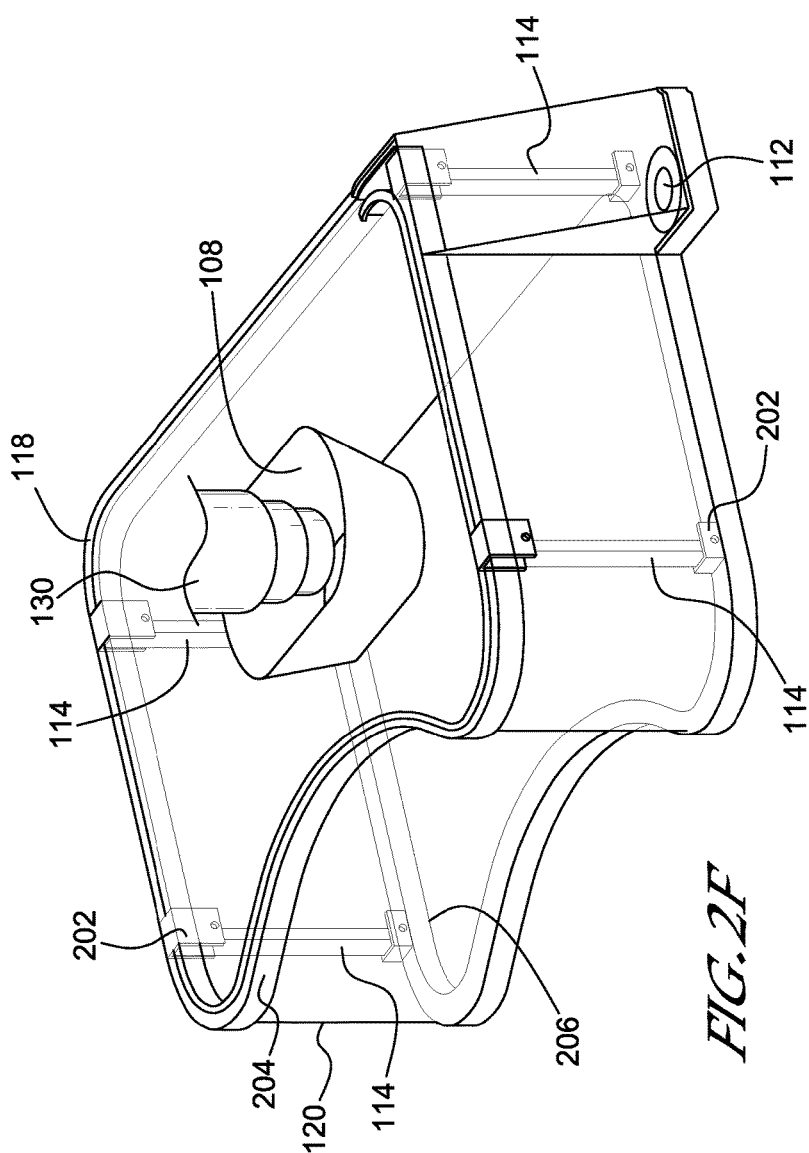
FIG. 2F. depicts an example of one embodiment of a drape and frame system of a sterile surgical drape system.

In some embodiments, the hole 108 can have a recess that extends in to the interior of the drape chamber, as shown in FIG. 2F. In some embodiments, the drape hole 108 can be perforated or have perforated cutouts in the drape material at the bottom of the recess. These perforations can allow for easy removal of the drape material that is over the operating area, allowing direct access and viewing of the surgical area with the microscope. For example, the microscope 130 can be placed over the hole 108 directly over the patient's surgical area, such as the eye. The recess in the hole 108 can have two sets of perforated cutouts at the bottom, one for the right eye and one for the left eye. The cutouts can be removed depending on which eye is being operated on. With the removal of this cutout, the microscope can have an unobstructed view of the eye during the surgical procedure.

Fan

Figure 1D:
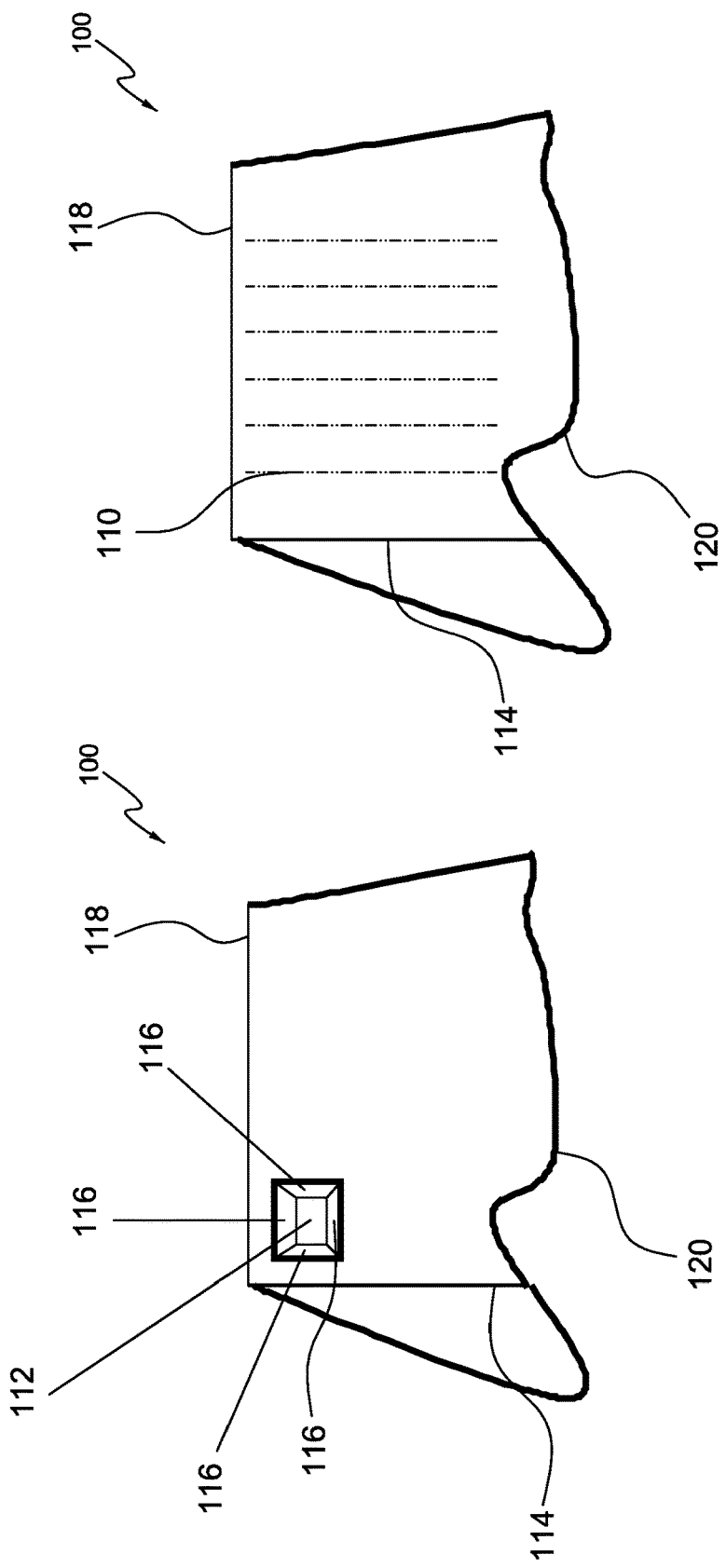
FIGS. 1D-1E. depict side views of an example of one embodiment of a sterile surgical drape system.
Figure 1E:
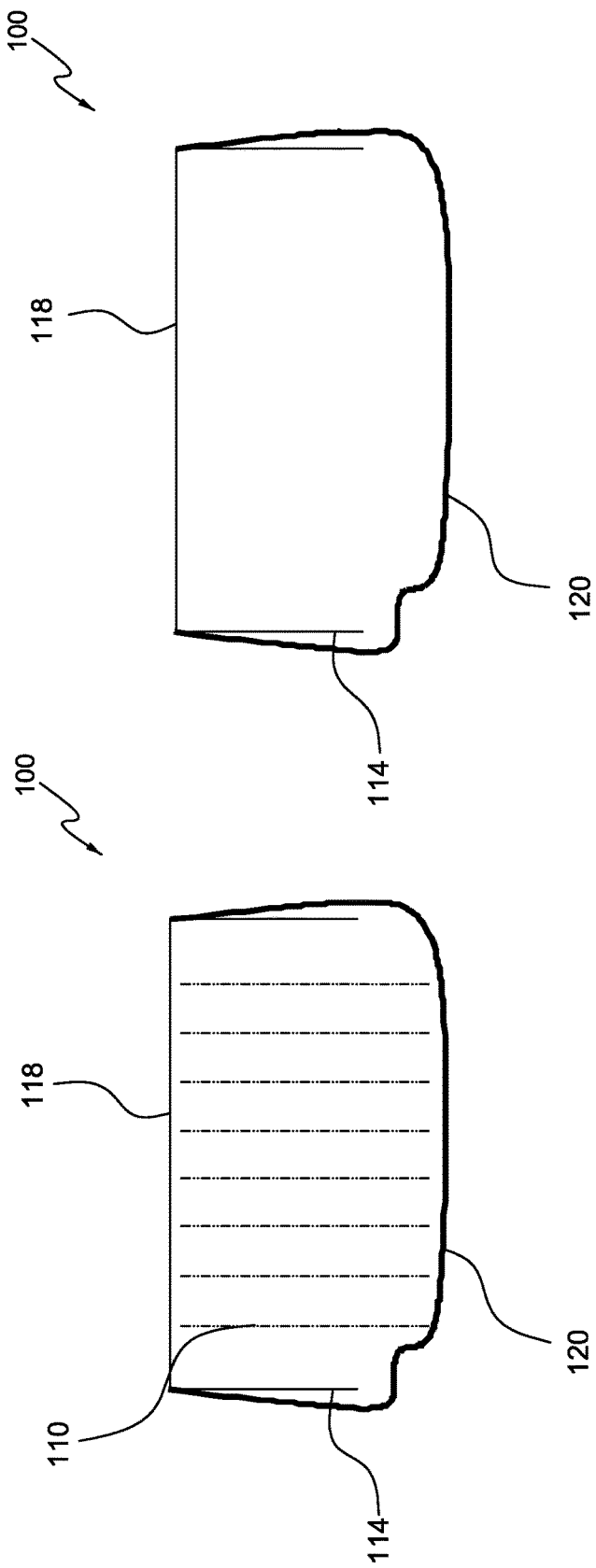
Figure 1F:
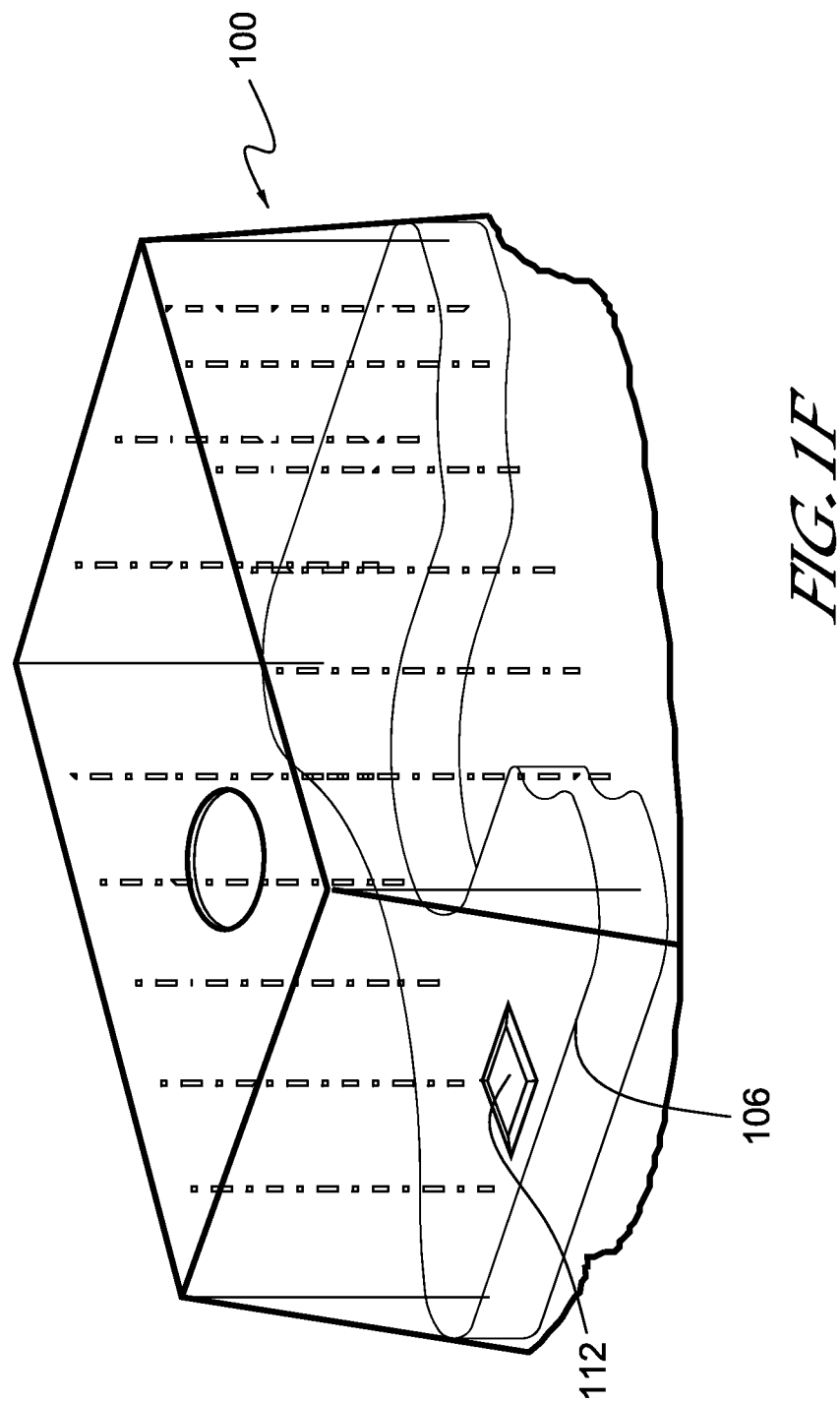
FIG. 1F. depicts an example of one embodiment of a sterile surgical drape system with a fan on the surgical tray.

In order to provide a sterile field underneath the drape 120, it can be advantageous to provide a steady pressurized air underneath the drape 120. The fan can operate in coordination with a filter which sterilizes or cleans the air entering the drape as described in detail herein. In some embodiments, the fan can be motorized. Accordingly, in some embodiments, an ophthalmic surgical drape system 100 comprises one or more pressurizing fans that draw air into the drape. In some embodiments, as shown in FIG. 1B-1D, the hole 108 can allow for a fan 112 to be positioned within the hole 108. The fan 112 can be sealed around it periphery in the hole 108 to prevent air from entering the surgical field.

In some embodiments, the fan 112 can be permanently attached to the drape system 100. The drape and frame system and the attached fan can be packaged and used as a single integrated unit. For example, the single integrated unit allows for the user to take the drape system out of the box, expand it, and place it over the surgical area, thereby simplifying the preparation and additional equipment traditionally necessary for the surgical procedure. Further, this integrated fan can eliminate the use of tubing or lines running from the drape system to a remote pressure source which can interfere with the surgeon during the surgical procedure. Additionally, the integrated fan allows for easy assembly and use of the system in the field or in a physician's office by reducing the amount of space occupied and the assembly required for an external fan or pressure source. For example, the user can simply attach the drape and frame system with the integrated fan to the tray with no additional assembly or attachment required. Also, the incorporated fan mitigates the need for the surgeon to have an expensive pressurization system in the physician's office. This system is also advantageous because it allows the surgeon to avoid using an expensive operating room because it is easily deployable in the field or in a physician's office while creating the necessary sterilized environment.

The fan 112 can be provided on a side or on the top of the drape 120. FIG. 1D illustrates side views of an example of one embodiment of a sterile surgical drape system 100. In the depicted embodiment, a fan 112 is located on the left side panel of an ophthalmic surgical drape system 100. In other embodiments, the fan 112 can be located on the right side panel of an ophthalmic surgical drape system 100 and/or any other panel. The location may depend on the inclination of the doctor or surgeon, who may, for example, want his or her assistant on the right or left side of the surgical drape. The left or right side panel of the surgical drape system 100 is defined as being the panels immediately adjacent to the panel in which a doctor or surgeon inserts his or her hands to perform a medical procedure while looking substantially down at a patient. In another embodiment, the fan can be located on the tray as illustrated in FIG. 1F. The fan can be integrated into the tray and provide the pressurized air to the chamber of the drape without additional holes in the drape. The fan can be configured to draw power from the tray. Additionally, an embodiment where the fan is integrated into the tray can simplify the design of the drape and the frame system. The fan can be positioned on the top and/or side surfaces of the tray. In some embodiments, the fan can also be positioned within the tray. In an embodiment, the sterilized air generated by the fan in the tray can be directed through channels in and/or on the tray to a plurality of ports positioned in various positions on the tray. The ports can be positioned on the side, outer parameter, and/or the top surface of the tray. The plurality of ports can allow for the sterilized air to be evenly distributed throughout the interior surgical chamber. In an embodiment, the plurality of ports can be configured to allow for the sterilized air to be directed in various directions within the interior surgical chamber. In an embodiment, the plurality of ports can be configured to more evenly distribute the delivery of sterilized air to the interior surgical chamber to mitigate possible harmful air current drafts during surgery.

In some embodiments, the fan 112 can be mounted to parts of the frame 118 as illustrated in FIG. 2A. The frame can have a lower rim 206 and an upper rim 204. In some embodiments, the lower rim 2006 can extend the full circumference of the drape system except the section in which the patient's head is to be provided. In some embodiments, the upper rim 204 can extend the full circumference of the drape system including the section that extends over the patient's body or head. In some embodiments, the fan 112 can be mounted to the lower rim of the frame 206 of the sterile ophthalmic surgical drape system and part of one or more legs 114 of the frame 118 of the sterile ophthalmic surgical drape system 100. The advantage of mounting the fan 112 in this position is that it does not result in weight being added to the upper rim of the frame 204 of the sterile ophthalmic surgical drape system 100. In other embodiments, the fan 112 can be mounted to the lower rim of the frame 206 of the sterile ophthalmic surgical drape system 100. In other embodiments, the fan 112 can be mounted to part of one or more legs 114 of the frame 118. In some embodiments, the fan can be mounted to the upper rim of the frame 204. In some embodiments, the fan 112 can be mounted to the upper rim 204 of the frame and part of one or more legs 114 of the frame 118.

In some embodiments, a fan 112 can be in electrical communication with the surgical tray 106 through a plug and access its power from the tray 106. In other embodiments, a sterile drape system 100 can have one or more battery sources from which the fan 112 may draw power. For example, one or more battery sources can be located inside one of the legs 114 of the frame 118 in the sterile drape system 100. In another example, one or more battery sources could be located on the upper rim 204 or lower rim 206 of the frame. In certain embodiments, a fan 112 may have one or more battery sources within the fan 112 from which it may draw power.

Additionally, in some embodiments, the air from the fan can be positioned or directed in a particular direction within the chamber by utilizing air directors 116. As illustrated in FIG. 1C, in some embodiments, the fan 112 can have one or more air directors 116 positioned adjacent to the fan 112. The air directors 116 can be positioned on either side, on the top, and/or on the bottom of the fan 112. The fan 112 may be positioned in one of many directions. In some embodiments, the fan 112 can be positioned in such a way as to provide airflow across a patient's eyes as described in detail herein. For example, FIGS. 1B-1D depict an example of one embodiment of positioning the fan 112 towards the edge of a leg 114 of the drape system 100. In other embodiments, the fan 112 may be positioned substantially in the center of the left or right panel of an ophthalmic surgical drape system 100. In some embodiments, the fan 112 may be positioned in between the edges of a leg 114 of the drape system 100.

In some embodiments, slits 110 can be provided on the drape 120 to allow for air within the chamber to be exhausted through the slits. In some embodiments, the slits can also be used by the surgeon or other user to insert their hands or tools into the drape chamber. Further, in some embodiments, the pressurized airflow provided by the fan 112 and air directors 116 can create a sterile surgical field within the chamber.

In some embodiments, even though the interior surgical chamber created by the drape 120 and frame 206 connected to the tray 106 is not fully sealed or closed off to the surrounding environment, a sterile field can be created in the interior surgical chamber by providing a steady and continuous pressurized airflow and environment within the interior chamber of the drape 120. The American Hospital Association (AHA) recommends that operating rooms keep air circulating at all times. The air within the operating room should not become stagnant because the lack of circulating air increases the risk of infection or contamination of the surgical site and/or surgical materials, especially in the context of ophthalmic surgery. The AHA has requirements for operating room ventilation and, according to the AHA, the rate at which the air must change in the room is approximately between 20 to 300 times per hour. In an embodiment, the airflow can be directed over the patient's face or across the patient's face and thereby meet the requirements for surgical procedures. The surgical drape system as described herein allows for airflow and a rate of exchange of air within the interior surgical chamber that can meet the forgoing air circulation requirements within the interior surgical chamber. The circulating air within the chamber as described herein can create a regulation compliant surgical area that can be used in a physician's office or in the field without the need for additional and expensive equipment or operating rooms equipped with the ventilation systems. The surgical drape system can create airflow generated by motorized fan, wherein the airflow is approximately 22 $m^2$ per hour, 24 $m^2$ per hour, 26 $m^2$ per hour, 28 $m^2$ per hour, 30 $m^2$ per hour, or 32 $m^2$ per hour.

Figure 1G:
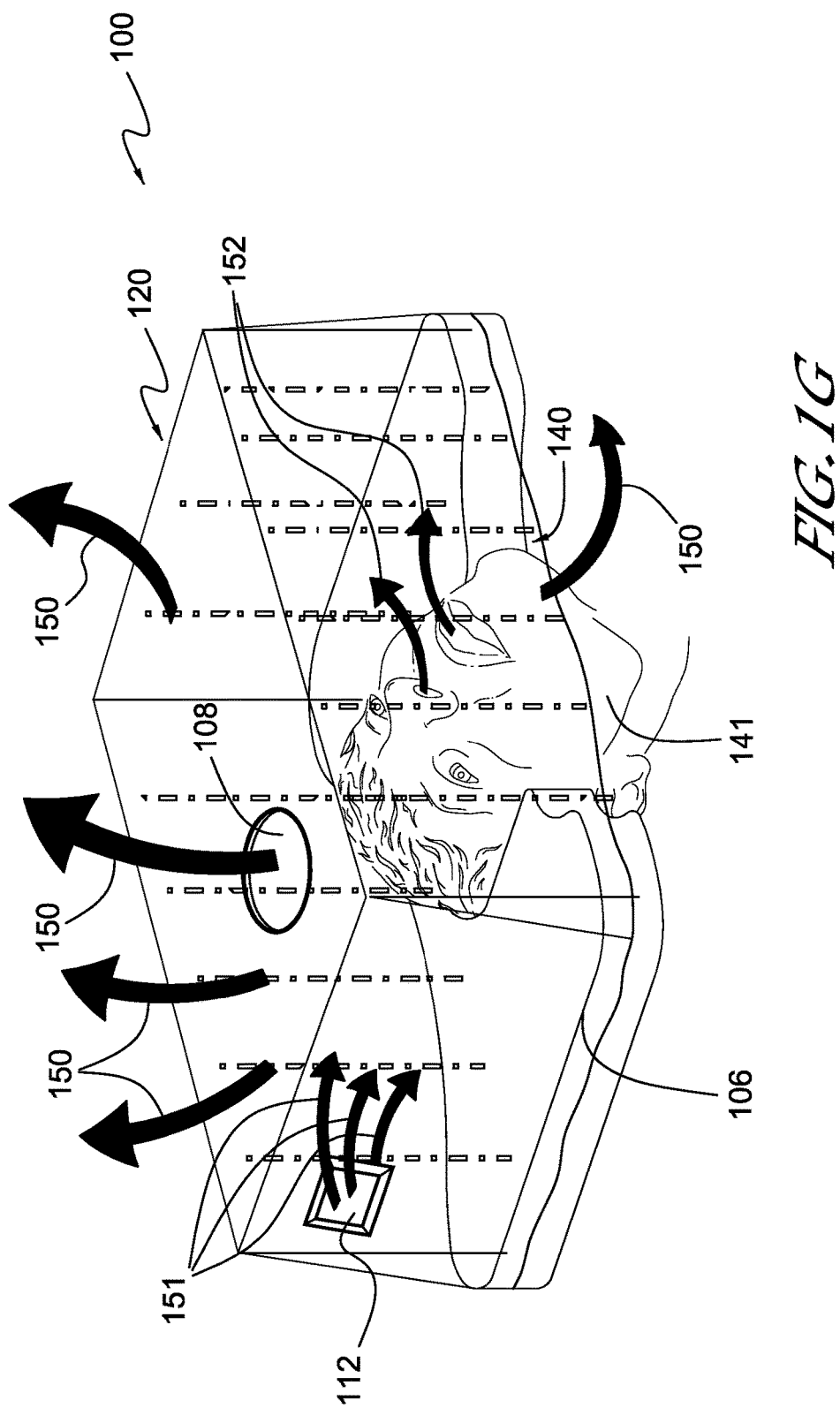
FIG. 1G. depicts an example of one embodiment of an airflow within a sterile surgical drape system with a fan.
Figure 1H:
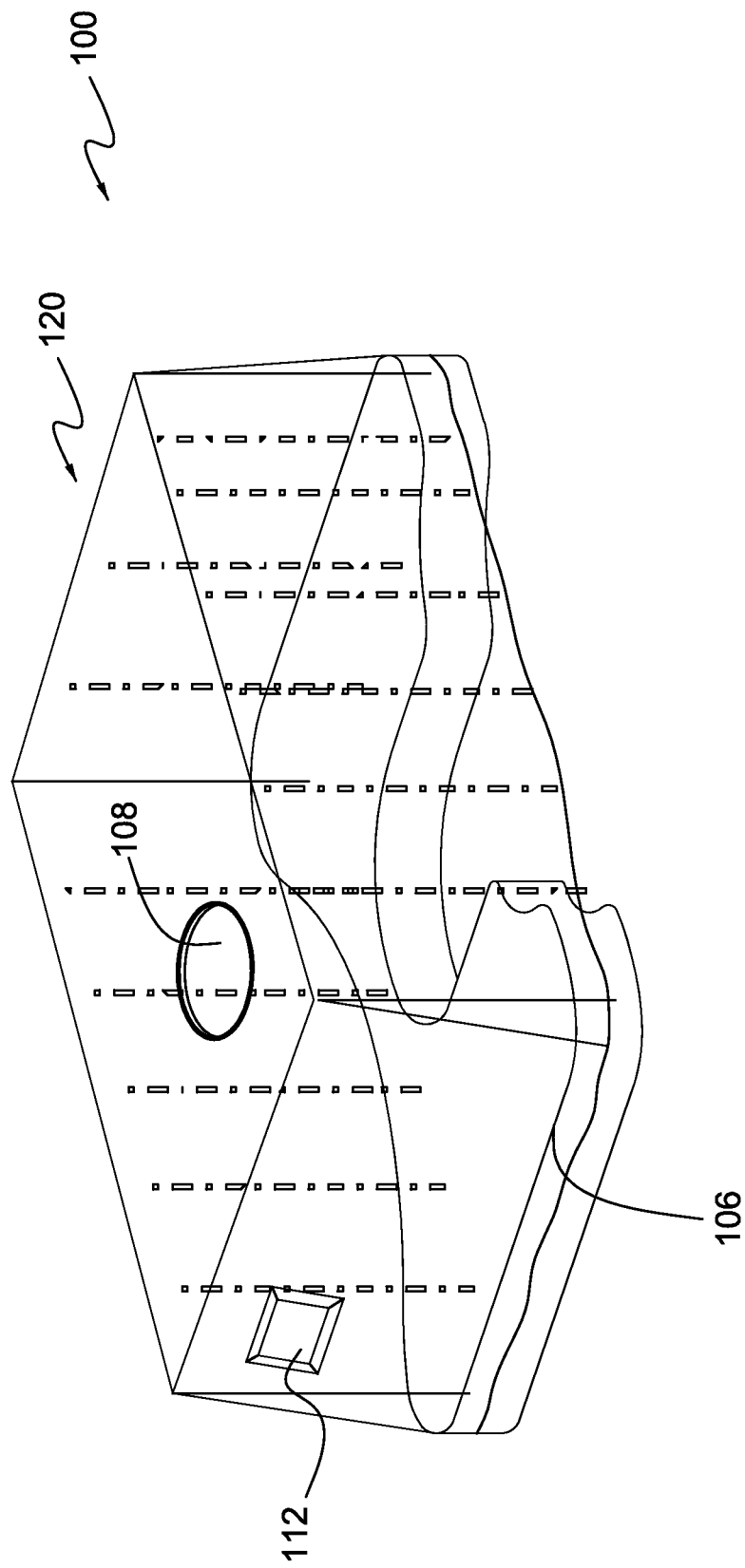
FIG. 1H. depicts an example of one embodiment of a sterile surgical drape system sealed to the surgical tray.

FIG. 1G illustrates an example of one embodiment of airflow within a sterile surgical drape system as generated by a motorized fan. In some embodiments, pressurized air 151 can be released into the chamber by the fan 112. The air 151 entering the chamber through the fan 112 can be filtered and the fan 112 can produce contaminant free and/or decontaminated air 151. During the surgical procedure, a patient 141 can release or exhale contaminated air from the nose and/or mouth 152 of the patient 141. The contaminated air can increase the risk of infection or contamination of the surgical site. The contaminated exhaled air 152 can be directed away from the surgical site of the interior chamber by allowing the exhaled air to flow out of the interior chamber through openings in the surgical drape system, as illustrated in FIG. 1G. The pressurized contaminant free airflow released by the fan 112 into the interior chamber can create a sufficiently high flow rate to force air within the drape 120 outward leaving the contaminant free filtered air within the drape 120. As shown in FIG. 1G, the air can flow out of the drape chamber through the hole 108, the area surrounding the patient's head 140, and the slits 110 and/or the openings for the hands of the surgeon, as depicted with airflow arrows 150 in FIG. 1G. The air movement and airflow can create a rate of air exchange within the drape that can meet operating room requirement.

Additionally, the creation of the pressurized environment creates an air pressure differential between the interior chamber of the drape and the ambient environment of the surgical room. This pressure differential is advantageous for a surgical procedure, in particular ophthalmic surgery, because it prevents ambient air from entering the interior chamber of the drape. In certain instance, the ambient air can comprise contaminants or other materials that can cause infection at the surgical site. The creation of the pressure differential prevents such contaminated air from entering the sterile surgical area of the drape. The pressure range for the pressurized airflow supplied from the fan can be about 0.5 psi, about 1 psi, about 2 psi, about 3 psi, about 4 psi, about 5 psi, about 6 psi, about 7 psi, about 8 psi, about 9 psi, and about 10 psi. In some embodiments, the pressure can be about 1 psi to about 2 psi.

The fan 112 can keep the drape pressurized so that there is an outgoing airflow from the interior of the drape system 100 to the surrounding area, with substantially no air flowing into the sterilized chamber except through the fan 112. By limiting the air entering the sterile chamber substantially to the fan 112, the fan 112 may prevent contaminants from entering the surgical site, for example a patient's eye(s), when the patient is in the sterile surgical field. In some embodiments, the fan 112 comprises one or more selectable velocities to provide a selectable amount of airflow in the closed chamber. The one or more selectable velocities of the fan 112 can be any value between 20-45 cubic feet per minute. In some embodiments, the fan 112 may keep enough air pressure in the chamber so that there is a substantially positive flow of air out of the drape system 100. In some embodiments, the fan 112 can be configured to generate laminar airflow.

In some embodiments, a drape system comprises more than one fan 112. In certain embodiments, the more than one fan 112 is positioned such that air flows in the same direction.

In certain embodiments, the drape system 100 comprises a vibration-free fan 112 to minimize vibration of the drape system 100. In some embodiments, the drape system 100 comprises a vibrating fan 112 coupled to vibration-absorbing material that is configured to minimize vibration of the drape system 100.

In some embodiments, the drape system comprises tubing instead of a fan. A tube, connected to an air source located outside of the sterilized chamber of a sterile ophthalmic surgical drape, can be inserted into an opening on the side panel of the ophthalmic surgical drape. An air source, for example sterilized air or oxygen, may be activated through the tubing. The air source may provide positive air pressure into the sterilized chamber and provide a substantially outward flow of air from the sterilized chamber to the external environment. Although both oxygen and sterilized air could be used, sterile air may be preferable to oxygen because oxygen may, in some instances, present a flammability risk.

Filter

In order to further provide and maintain a sterile field, it can be advantageous to install one or more air filters to the drape system to substantially prevent contaminants from entering the chamber in which the procedure is being performed. Accordingly, in some embodiments, the drape system comprises one or more air-cleaning filters attached and/or coupled to the various embodiments of the fan as disclosed herein. For example, the filter can be a High-Efficiency Particulate Air ("HEPA") filter or the like. In certain embodiments, the one or more filters that can be installed can be HEPA filters with efficiencies of at least approximately 99.97 percent on all airborne particulate matter 0.3 micron in diameter and larger.

In some embodiments, a cross-sectional area of the one or more filters is substantially equal to a cross-sectional area of the fan. In certain embodiments, a cross-sectional area of the one or more filters is larger than a cross-sectional area of the fan.

In some embodiments, one or more filters may be located on the exterior side of the fan. In certain embodiments, one or more filters may be located on the interior side of the fan. In other embodiments, one or more filters may be located in between the exterior and interior sides of the fan.

Air Director

In embodiments where the drape system 100 comprises one or more fans 112, it can be envisioned that airflows with different paths may be preferred for different patients and/or situations. Accordingly, in some embodiments, the airflow of one or more fans 112 of a sterile ophthalmic surgical drape system 100 is adjustable. FIGS. 1B-1D illustrate embodiments of a fan 112 with one or more air directors 116.

In certain embodiments, a drape system 100 comprises one or more air directors 116 coupled to one or more fans 112. For example, the one or more air directors 116 can be attached to the one or more fans 112 in the interior and/or exterior of the drape system 100. In some embodiments, the one or more air directors 116 can allow a user, for example a doctor, surgeon, nurse, or assistant, to control the air directors 116 from inside the drape system 100. In other embodiments, the fan 112 is controllable on the outside by, for example, the doctor or surgeon's assistant. The control of the airflow direction can allow the surgical drape system to provide an airflow or pressurized airflow across the surgical field, for example the patient's face that satisfies the operating room requirements discussed herein.

Slits

FIGS. 1B-1E depict an example of one embodiment of a sterile ophthalmic surgical drape system 100 with substantially vertical slits 110 in the panels of the drape 120. In other embodiments, the slits 110 in the panels of the drape 120 may be oriented in one of many positions such as substantially horizontal or diagonal. The slits 110 can be configured to allow the airflow within the drape to exit. In some embodiments, the drape 120 comprises one or more outlets to allow the airflow generated by a fan(s) to exhaust.

In some embodiments, the one or more slits 110 are further configured to allow a user to insert his or her hands into the sterile field. In some embodiments, as depicted in an example in FIGS. 1B, 1C, and 1E, there may be one or more slits 110 in the panel of the drape 120 that face the surgeon. For example, the panel of the drape 120 that faces the surgeon can comprise two slits so the surgeon can insert both hands into the drape.

FIG. 1C depicts an example of an embodiment in which there are no slits on a top panel with a hole of sufficient size for a microscope 108. However, in other embodiments, there may be one or more slits 110 in the top panel.

FIG. 1D depicts an embodiment in which there are no slits down the side panel of the drape system 100 that contains the fan 112. In other embodiment, there can be one or more slits 110 in the side panel of the drape system 100 that contains the fan 112. In some embodiments, the side panel of the drape system 100 where the fan 112 is located comprises one or more holes to allow air to flow into the fan.

On the side opposite of the panel with the fan 112, there can be one or more slits 110. The slits can allow a user, such as an assistant or nurse, to reach his or her hands into a sterile chamber to assist, for example, a doctor or surgeon.

Looking to FIG. 1E, the panel opposite to the panel facing a doctor may provide no slits where the patient's head rests beneath the drape system 100 and surgical tray 106. In other embodiments, the panel opposite to the panel facing a doctor may have one or more slits 110.

In some embodiments, the one or more slits 110 in one or more panels of a sterile ophthalmic surgical drape 120 extend substantially to the bottom of the surgical drape 120. In other embodiments, the slits do not extend substantially to the bottom of the surgical drape 120.

Frame

It can be advantageous for a drape system to comprise a frame or other rigid structure to maintain the drape's position over a patient and to provide sufficient space for a surgeon or other medical professional to work. Accordingly, in some embodiments, a drape system comprises a frame with the drape located over the frame.

A frame apparatus 118 of an ophthalmic surgical drape system 100 can be a sterile frame that has been manufactured and assembled as a prepackaged sterile frame comprising, among other materials, injection-molded, acrylonitrile butadiene ("ABS") plastic. In certain embodiments, the frame 118 can be substantially transparent to allow for better visualization of the surgical area.

The frame 118 can have one of many different shapes. For example, the frame 118 can be substantially spherical, pyramidal, conical, or rectangular. FIG. 2A-2F depict an embodiment in which the frame 118 is substantially rectangular. In another embodiment, the upper rim of the frame 204 may have increased curvature to provide a user with additional vantage points so the user may view a patient from a position other than directly below the user.

FIGS. 2A-2F illustrate an example of one embodiment of a frame apparatus 118 of an ophthalmic surgical drape system 100. The frame 118 can be configured to allow the frame and drape to be attached to a surgical tray. The frame can have an upper rim 204, a lower rim 206, and legs 114. The drape can be provided over the upper rim 204 of the frame 118. In some embodiments, when the frame is in the expanded configuration, the legs 114 have a distal end located farthest from the patient and a proximal end located closest to the patient as illustrated in FIG. 2A. The distal end of the legs 114 are configured to contact the upper rim 204 of the frame when in the expanded configuration. The upper rim 204 and the legs 114 provide the support for the surgical drape. The proximal end of the legs 114 are configured to connect to the lower rim 206 of the frame when in the expanded configuration. The lower rim 206 can attached to a surgical tray as described herein.

In some embodiments, the upper rim 204 and the lower rim 206 can have the same or substantially the same circumference as the surgical tray. In some embodiments, the upper rim 204 and the lower rim 206 can have a smaller or larger circumference than the surgical tray. In some embodiments, the upper rim 204 and the lower rim 206 can have substantially the same circumference. In other embodiments, the upper rim 204 and the lower rim 206 can have a substantially different circumference. FIG. 2A depicts an embodiment in which the lower rim of the frame 206 may extend all around the circumference of a surgical tray 106 to which it may be connected, except where a patient positions his or her head. The upper rim of the frame 204 may extend all around the circumference of the tray 118, including where the patient positions his or her head.

The frame 118 can comprise one or more substantially vertical legs 114. In certain embodiments, one or more legs 114 can connect a lower rim of the frame 206 to an upper rim of the frame 204. For example, in FIG. 2A, four legs 114 connect the lower rim of the frame 206 to the upper rim of the frame 204.

In some embodiments, the frame 118 may be collapsible. The frame 118 may be manufactured and shipped in a collapsed configuration in a package from a manufacturer to a customer, such as a hospital, doctor's office, military location, or the like. The package may be a pre-sterilized package. For example, the package may be sterilized through an ethylene oxide sterilization process. FIG. 2C depicts an example of one embodiment of a frame apparatus 118 in its collapsed form. When a frame 118 is collapsed, the upper rim of the frame 204 and the lower rim of the frame 206 can be substantially in contact with each other.

In some embodiments, to apply the frame 118, a party may connect the frame apparatus 118 to a surgical tray 106 and raise the upper rim of the frame 204. As shown in FIGS. 2A and 2B, the one or more legs 114 rise and lock in a substantially upright, vertical position to secure the frame apparatus 118. The one or more legs 114 connect the lower rim of the frame 206 to the upper rim of the frame 204 at hinges 202 located on the lower rim of the frame 206.

In some embodiments, to disassemble the frame apparatus 118, the frame apparatus may be disconnected from the surgical tray 106 or tray support 104 or the like. A party may apply a force to the frame apparatus to unlock the one or more legs 114 at the hinges 202 connecting the lower rim of the frame 206 to the upper rim of the frame 204. The one or more legs 114 of the frame apparatus 118 may fold in one of many different directions. For example, as illustrated in FIG. 2C, the one or more legs may fold in a substantially inward direction relative to the frame apparatus 118. Alternatively, the one or more legs may fold in a substantially outward direction relative to the frame apparatus 118.

In other embodiments, the hinges 202 may be located in between the two ends of the one or more legs 114. For example, FIGS. 2D-2F depict an example of one embodiment of a frame apparatus 118 in which the hinges 202 may be located substantially at the center of one or more legs 114. The hinge 202 can operate as described herein with reference to FIG. 2G.

FIG. 2F illustrates an example of an embodiment of a frame 118 with a drape 120 disposed over the frame in an expanded configuration. The frame can have an upper rim 204, a lower rim 206, and legs 114 there between as described in detail herein. Further, in some embodiments, the legs 114 can connect to the upper rim 204 and the lower rim 206 with attachment mechanisms such as hinges 202 or other attachment mechanisms as described herein. In some embodiments, the hole 108 can be positioned in the center of the drape to allow for access of surgical tools or accessory devices, such as a microscope, a fan, or other surgical tools as described herein. Additionally, in some embodiments, the drape and frame system can have a fan 112 that can allow for controlled access of airflow into the chamber.

Figure 2G:
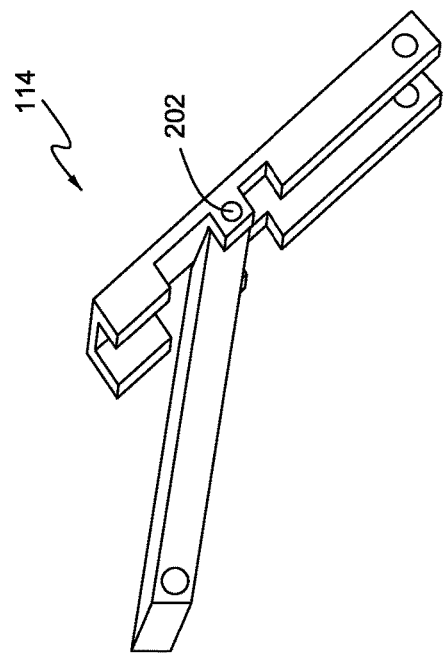
FIG. 2G. depicts an example of one embodiment of a leg of a frame of a sterile surgical drape system.
Figure 2G:
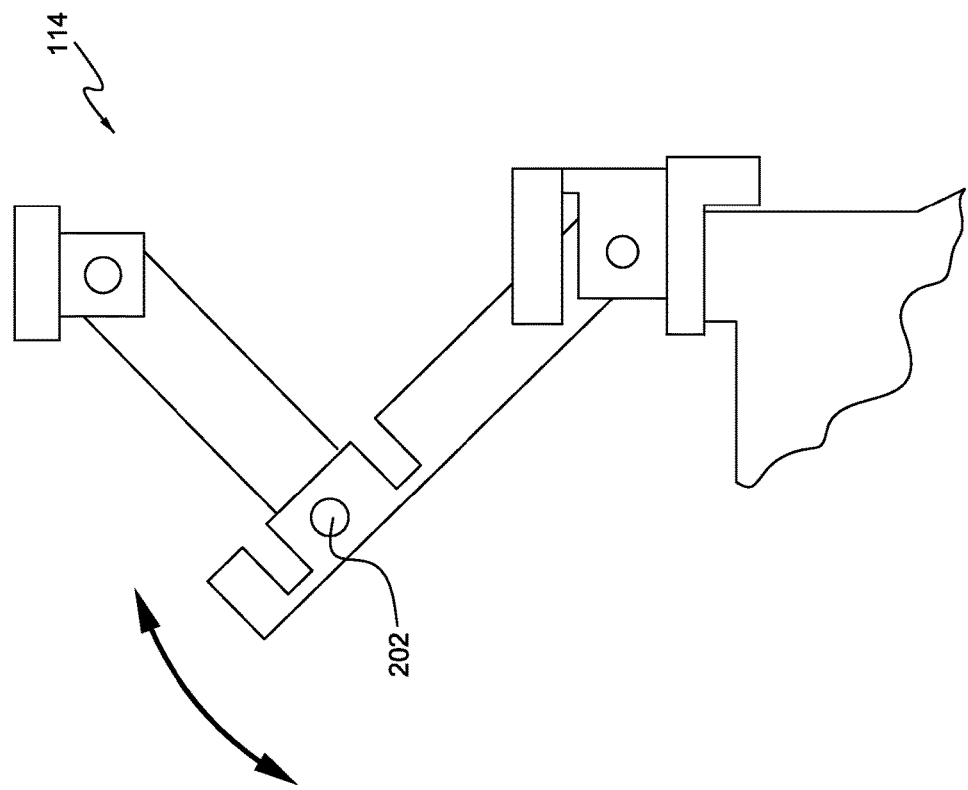

FIG. 2G illustrates an example of an embodiment in which the one or more legs may be deformable. The legs 114 may bend or fold to allow the frame to collapse or fold. This deformable leg allows the frame to be easily moved and/or stored. In some embodiments, the legs 114 may fold at the hinges 202, which may be located substantially at the center of the one or more legs 114. The legs 114 may fold in a substantially inward direction relative to the frame apparatus 118. In other embodiments, the one or more legs 114 may fold at the hinges 202 that may be located substantially at the center of the one or more legs 114, in a substantially outward direction relative to the collapsed frame apparatus 118. The hinge 202 in the center of the legs 114 allows the frame to be fully collapsible and expandable with the legs folded between the lower rim and the upper rim of the frame. The hinge 202 in the leg can allow for the frame to collapse into a flat configuration without the need for detaching a portion of the leg 114 from either the upper or lower rim. The legs 114 can therefore remain permanently secured to the frame. This provides the surgeon with an easily expandable and collapsible sterile surgical field that can be expanded in an office or in the field without the need for additional tools to secure the legs 114 to the frame.

In some embodiments, a frame 118 may be manufactured and shipped in a configuration in which a lower rim of the frame 206 and one or more legs 114 that can connect the lower rim 206 to an upper rim 204 are attached to a surgical tray 106. The frame may be pre-sterilized. To apply the frame, in some embodiments, the upper rim of the frame 204 may be separately attachable to the lower rim of the frame 206 and the one or more legs 114 that can connect the lower rim 206 to the upper rim 204.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Although the embodiments of the inventions have been disclosed in the context of a certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or subcombinations of the specific features and aspects of the embodiments may be made and still fall within one or more of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above.

What is claimed is:

1. A device for performing surgery comprising:
    a drape, the drape comprising a first hole configured to allow at least one accessory device to be placed in the first hole and to access a surgical site covered by the drape;
    a frame comprising:
        an upper rim,
        a lower rim, and
        four legs, wherein each of the four legs couple to the lower rim using a first hinge, couple to the upper rim using a second hinge, and include a third hinge in between the first hinge and the second hinge, the frame configured to be collapsible from a collapsed configuration in which the upper rim and the lower rim are substantially in contact with each other to an expanded configuration in which the four legs lock in a vertical position to separate the upper rim and the lower rim, the frame moving from the collapsed configuration to the expanded configuration by rotating each of the four legs at the first and second hinges and folding each of the four legs at the third hinge in an inward direction, wherein the drape is configured to be coupled to the frame to define an interior surgical chamber;
    a motorized fan positioned within a second hole in the drape, the motorized fan configured to generate pressurized airflow within the interior surgical chamber, the motorized fan comprising a filter, the filter configured to filter out contaminants from the pressurized air, wherein the pressurized airflow generated by the motorized fan creates an air pressure differential that ranges between 0.5 psi and 10 psi between the interior surgical chamber and ambient environment outside the interior surgical chamber;
    an airflow director configured to adjust a direction of the pressurized airflow within the interior surgical chamber, the airflow director controllable by a user from inside the interior surgical chamber to change the direction of the pressurized airflow based on a requirement of a surgical procedure; and
    a surgical tray coupled to the lower rim, wherein the drape is coupled to the surgical tray, wherein the surgical tray is configured to be releasably attached to the drape, wherein the surgical tray comprises a power source for powering the motorized fan.

2. The device of claim 1, wherein the at least one accessory device comprises a microscope.

3. The device of claim 1, wherein the second hole is positioned on a side portion of the drape and the motorized fan is coupled to at least one portion of the frame.

4. The device of claim 1, wherein the second hole is positioned on a top portion of the drape and the motorized fan is coupled to at least one portion of the frame.

5. The device of claim 1, wherein the motorized fan comprises an air director, wherein the air director is configured to adjust the direction of an airflow of the motorized fan.

6. The device of claim 1, wherein the drape further comprises at least one slit.

7. The device of claim 1, wherein the surgical tray is further configured to substantially form a seal between the drape and the surgical tray along one or more edges of the surgical tray.

8. The device of claim 1, wherein the surgical tray is configured to be coupled to a tray support.

9. The device of claim 8, wherein the tray support comprises a support bar, wherein the surgical tray is configured to be coupled to the support bar.

\* \* \* \* \*